US005821066A

United States Patent [19]
Pyle et al.

[11] Patent Number: 5,821,066
[45] Date of Patent: Oct. 13, 1998

[54] SIMPLE, RAPID METHOD FOR THE DETECTION, IDENTIFICATION AND ENUMERATION OF SPECIFIC VIABLE MICROORGANISMS

[75] Inventors: Barry H. Pyle, Belgrade; Gordon A. McFeters, Bozeman, both of Mont.

[73] Assignee: The Research & Development Institute, Inc., Bozeman, Mont.

[21] Appl. No.: 858,707

[22] Filed: May 19, 1997

Related U.S. Application Data

[63] Continuation of Ser. No. 245,262, May 18, 1994, abandoned.

[51] Int. Cl.$^6$ .................................................. G01N 33/53
[52] U.S. Cl. ............................... 435/7.2; 435/29; 435/30; 435/34; 435/174; 435/176; 435/177; 435/180; 436/518; 436/525
[58] Field of Search .............................. 435/7.1, 7.2, 29, 435/30, 34, 174, 176, 177, 180; 436/518, 525

[56] References Cited

U.S. PATENT DOCUMENTS

| | | |
|---|---|---|
| 4,693,972 | 9/1987 | Mansour et al. . |
| 4,925,789 | 5/1990 | Edberg . |
| 4,959,301 | 9/1990 | Weaver et al. . |
| 4,972,258 | 11/1990 | Wolf et al. . |
| 5,173,187 | 12/1992 | Nader et al. . |
| 5,256,532 | 10/1993 | Melnicoff et al. . |
| 5,268,486 | 12/1993 | Waggoner et al. . |

OTHER PUBLICATIONS

Shama et al, Applied and Environmental Microbiology, Jun. 1993 59(6): 1864–1875.
Cloette et al, Water Research, 1988, 22(8): 961–969.
Desmonts et al, (Applied & Environmental Microbiology, May 1990, 56(5): 1448–1452.
Desmonts et al., J. Microbiology Methods, 1992, 16: 195–202.
Weir et al eds., Handbook of Experimental Immunology in Four Volumes, vol. 1: Immunochemistry, published 1986 by Blackwell Scientific, Boston (MA) pp. 27.1–27.20.
Singh et al, Journal of Microbiology Methods, 1989, 10: 91–101.
Kaprelyants et al, Journal of Applied Bacteriology, 1992, 72: 410–422.
Vermont et al., Journal of Applied Bacteriology, 1992, 72: 112–118.
Terstappen et al (Cytometry, 1988, 9: 477–484).
Olsvik et al (Clinical Microbiology Reviews, Jan. 1994, 7(1) 43–54.
Rodrigues, G.G. et al., "Use of a Fluorescent Redox Probe for Direct Visualization of Actively Respiring Bacteria," Applied and Env. Microbiology, vol. 58, No. 6, Jun. 1992, pp. 1801–1808.
Schaule, G. et al., "Use of 5–Cyano–2,3–Ditylyl Tetrazolium Chloride for Quantifying Planktonic and Sessile Respiring Bacteria in Drinking Water," Applied and Environmental Microbiology, vol. 59, No. 11, Nov. 1993, pp. 3850–3857.
Chemical Abstracts, vol. 100, 1984, p. 292.
Chemical Abstracts, vol. 87, 1977, p. 434.
Chemical Abstracts, vol. 102, 1985, p. 281.

*Primary Examiner*—Paula K. Hutzell
*Assistant Examiner*—Patricia A. Duffy
*Attorney, Agent, or Firm*—McDermott, Will & Emery

[57] ABSTRACT

A rapid method for the detection, identification and enumeration of specific respiring microorganisms. The method includes steps of a) passing a microbial sample through a collecting device to capture the cells; b) adding to the collecting device a fluorochrome dye specific for the detection of respiring cells and allowing the dye to incubate; c) treating the collecting device with a reactive fluorescent antibody which reacts with a target microorganism of interest present in said microbial sample; d) mounting the collecting device for examination by fluorescence microscopy in which a suitable light system is used to excite the fluorochrome dye and fluorescent antibody to fluoresce; and e) quantifying the respiring cells. Alternative embodiments include the use of immunomagnetic beads and other means of cell capture, and employing fluorescent oligonucleotide probes rather than fluorescent antibodies.

19 Claims, 2 Drawing Sheets

SIMPLE, RAPID METHOD FOR THE DETECTION, IDENTIFICATION AND ENUMERATION OF SPECIFIC VIABLE MICROORGANISMS

This application is a continuation of application Ser. No. 08/245,262 filed May 18, 1994, now abandoned.

TECHNICAL FIELD

The present invention relates to the field of methods of detection, identification and enumeration of respiring microorganisms.

BACKGROUND

The detection, identification and enumeration of individual respiring bacteria or other microorganisms is important to and widely used in biological research, clinical microbiology, cancer diagnosis and treatment, environmental science, food safety, toxicology, and research and development in basic and applied biology.

Specifically, in public health and environmental microbiology, there is a need for rapid methods to enumerate and identify specific viable bacteria and other microbes. In foods, robust, reliable testing methods are needed that provide results more rapidly than conventional methods, with similar or greater sensitivity and specificity. This requirement is also of particular concern in relation to water which is reclaimed for potable use, such as on the U.S. Space Station.

There is also a dramatic increase in the number of cases of food-borne *Escherichia coli* in recent years and the prevalence of meat samples which are contaminated with these organisms suggest a need for rapid, specific bacterial detection methods. Conventional methods may grossly underestimate the numbers of specific target bacteria in a sample. One of the obstacles to the development and application of rapid, direct methods for the detection of specific pathogenic bacteria in foods is the need to concentrate the target bacteria and separate them from suspensions of the product. It is normally required that a contaminant should be detectable at less than 1 colony forming unit per 25 g sample. Filtration is usually avoided because it is not possible to filter large samples of meat homogenate even after large particles have been allowed to settle out.

The need for such a method and problems associated with known methods for detection, identification and enumeration of viable bacteria are set forth in Weaver et al., U.S. Pat. No. 4,959,301, incorporated herein by reference. Present methods for enumeration of viable microorganisms are slow and generally labor intensive, and many newer methods which purport to give an enumeration are not based on actual viable cell counts.

Instead, many of these methods measure some average property of a large number of cells which, under well defined conditions, correlates with a count, but which under other conditions generally does not correlate accurately with a viable count.

Present cell analysis methods involve two major classes of assays. The first class rapidly detects and identifies specific cells directly from a primary sample, but does not determine cell viability. The most widely used in this class are specific ligand binding assays, e.g. immunoassays and genetic probes. However, they require many cells, and do not distinguish between dead and viable cells. This restricts their use to samples in which sufficient numbers of cells are present, and to determinations in which direct assessment of the physiological state of the cell is irrelevant.

The second class of assays is used for viable cell determinations either directly using the primary sample, or using a subculture of the primary sample. The most traditional and widely used method is the plate count, which allows determination of single cell viability, based on growth, under many test conditions (see, for example, Hattori The Viable Count: Quantitative and Environmental Aspects, Brock/Springer, Madison, 1988). An important attribute of viable plate enumeration is that the time required to obtain a determination is independent of the concentration of the cell in the sample, as formation of each colony proceeds from an initial single cell. The major disadvantage is its slowness, as typical determinations require one-half to several days, and are also labor- and materials-intensive.

The disadvantages of viable plating can better be appreciated by drawing attention to its basic attributes. Viable plating is a well established, important method for qualitatively determining the growth of cells, particularly the presence or absence of growth for given conditions, and is often based on the growth of initial cells into distinct colonies. Viable plating typically involves the spreading of a suspension of cells onto the surface of a gel-containing petri dish, with or without the pouring of a gel layer over the first gel surface.

The gels are provided with nutrients, such that following an incubation period at a suitable temperature, many generations of growth occur, which leads to formation of visible colonies. For many microorganisms formation of visible colonies requires growth for 22 to 30 generations and therefore produces colonies containing $10^7$ to $10^9$ cells. (See Sharpe, in Mechanizing Microbiology, A. N. Sharpe and D. S. Clark (Eds.) Charles C. Thomas, Springfield, 19–40, 1978). Although conventional viable plating leads to formation of colonies, and thereby provides a basis for counting viable cells by counting colonies, the presence or absence of colonies only allows an inference that the conditions present in the gel do or do not support growth. For this reason, conventional viable plating is not well suited to quantitative determinations such as cell growth rate and lag time, because viable plating based on visual inspection counts the number of colonies formed, but does not determine how the cellular material or amount of cellular constituents in the colonies varies with time.

An additional complication arises because the nutrient and metabolite concentrations within a colony comprise a microenvironment, which generally changes with time in a variable way as microcolonies increase to form larger colonies with many cells in close proximity. The microenvironment within a large colony can also have significant heterogeneity of chemical composition within the microcolony, so that different cells within a large colony experience different growth conditions. Further, although some methods are based on a straightforward extension and application of scanning optical methods for determination of optical properties of colonies on or in gel slabs, such methods suffer from relatively large cost, and, because of the relatively large gel slab size, does not allow incubation conditions to be changed rapidly at the site of the cells within the gel. (See Glaser in New Approaches to the Identification of Microorganisms Proceedings of a Symposium on Rapid Methods and Automation in Microbiology, C. G. Heden and T. Illeni (Eds.), Wiley, N.Y., 3–12, 1975).

There are other limitations of plating techniques which may lead to underestimation of bacterial numbers. These include the possibility of bacterial clumping or attachment to particles in the sample. When this occurs and cells are not disaggregated or dislodged from particles, the assumption that a colony arises from a single cell is invalidated. Another consideration is the injury of bacteria by a variety of stressors which occur in water (McFeters, G.A. 1990. Enumeration, occurrence, and significance of injured indicator bacteria in drinking water, in Drinking Water Microbiology, McFeters (ed.), Springer-Verlag, New York, pp. 478–492) and food (Ray, B. (Ed.) 1989. Injured Index and Pathogenic Bacteri: Occurrence and Detection in Foods, Water and Feeds. CRC Press, Boca Raton).

Instrumented methods for rapidly determining cell or culture growth and/or metabolic activity have been developed which only partially address the limitations of the viable plate assay. These include optical techniques for growth determination such as those which measure the change in light scattering due to many cells in a liquid suspended culture (See, for example, Edberg and Berger, in Rapid Methods and Automation in Microbiology and Immunology, K. O. Habermehl, Ed., Springer-Verlag, Berlin, 215–221, 1985), and a variety of metabolic activity based techniques which measure changes due to many cells in an analyzed sample. Examples include changes in extracellular pH, electrical impedance or fluorescence.

A disadvantage of all such metabolic activity methods is that they are based on combined effects of a large number of cells, and therefore generally require an initial process, based on plating, to obtain initial colonies for purposes of inoculation of the analyzed sample, such that the determinations based on many cells at least are based on a monopopulation, i.e. a population comprised nominally of the same type of cells. For this reason, although a total population cell determination may itself be rapid, it is generally preceded by a viable plating method, or its equivalent, which is slow. Thus, the total analysis time, counted from receipt of a primary or non-plated sample to a cell growth determination, is the sum of both, and therefore still long.

Further, because such determinations are based on the combined effect of a large, but unknown number, of cells, such total population determinations do not actually yield a count. In contrast, determinations based on many individual measurements, each associated with an initial single cell, can yield a count.

Finally, because these total population methods are based on the combined effects of many cells, the time required for a determination becomes significantly longer as the number of cells decreases, i.e. as the sample's cell concentration decreases.

Similarly, prior use of flow cytometry for cell growth measurements (see, for example, Hadley et al. in Instrumental Methods for Rapid Microbiological Analysis, Nelson (Ed.), VCH, Weinheim, 67–89, 1985) is limited, because conventional use of flow cytometry performs measurements on individual cells, or clumps of cells which naturally adhere, in an aqueous liquid suspension, and therefore does not have the capability to measure colony formation. For this reason, prior use of flow cytometry can only measure total numbers of cells in a volume in order to determine average growth, and must also, therefore, involve a careful volume measurement, and is dependent on the signal-to-noise ratio of single cell measurements. This signal-to-noise ratio is less than satisfactory for many measurements (see, for example, Shapiro Practical Flow Cytometry, R. Liss, New York, 1985; Hadley et al. in Instrumental Methods for Rapid Microbiological Analysis, Nelson (Ed.), VCH, Weinheim, 67–89, 1985).

Likewise, quantitative microscopy and image analysis combined with conventional gel preparations, such as gel slabs, petri dishes and the like, although capable of determining colony formation, is tedious, and in manual versions, conventional gel slabs, petri dishes and the like, cannot provide physical manipulability or a sufficiently fast (small) characteristic diffusion time within the gel, so that cells cannot be rapidly and conveniently exposed to different growth conditions, such as rapid changes in concentrations of nutrients, drugs, hormones, enzymes, antibodies and other chemicals. In addition, conventional gel slabs, petri dishes and the like cannot be readily manipulated physically because of their size, and therefore cannot be readily used for exposure of gel-entrapped cells to in vivo conditions.

Mansour et al., U.S. Pat. No. 4,693,972 teaches a composition and method for rapid detection of microorganisms in clinical samples. The method for detection of microorganisms in a body fluid sample includes detecting a microorganism after treatment of the sample with a lysing agent in order to dissolve sample components other than microorganisms, and staining with a fluorescent dye.

Wolf et al., U.S. Pat. No. 4,972,258 discloses a scanning laser microscope system and methods of use. The patent discloses a yeast culture was placed on a black polycarbonate filter. The filter was then overlaid with a fluorescent stain. The filter was rinsed in a succession of steps and then the filter was air dried and placed on top of a glass microscope slide. The fluorescent stain is an indicator of viability and direct staining of microorganisms may be used for detection and enumeration and analysis of the microorganisms. The patent also discloses an indirect immunofluorescence assay in which a target microorganism is labelled with a primary non-conjugated antibody specific for microorganisms containing a target surface antigen. The microorganisms with bound antibody are fluorescently labelled using a fluorescein isothiocyanate conjugated secondary antibody which recognizes the primary antibody. Then the labelled microorganisms are placed on an appropriate surface and imaged using a scanning laser microscope. A filter is used which reflects the laser light and passes the fluorescence light. Wolf et al. does not disclose using 5-cyano-2,3-ditolyl tetrazolium chloride (CTC) to detect respiring bacteria.

Weaver et al., U.S. Pat. No. 4,959,301 teaches a process for rapidly enumerating viable entities. The patent describes the method of enumeration of viable biological entities which involves the determination of the number of viable biological entities per volume. The patent also discloses a method of determining the number of viable biological entities capable of growth per volume of a sample, comprising a) forming microdroplets of a volume of the sample wherein some but not all of the microdroplets contain viable biological entities; b) measuring the volumes of at least a portion of the microdroplets formed in step (a) to obtain the volumes of the microdroplets; (c) measuring the amount of biological material which constitutes part of the viable biological entities in the microdroplets and d) determining the statistical distribution of the biological material in the droplets and the volumes as indicative of the number of viable biological entities per volume of the sample. The measurement of the biological material accumulated within the microdroplets was enhanced after incubation with fluorescent stains. The microdroplet volumes are measured optically and the optical means consist of light scattering, light absorbance, fluorescence, phosphorescence or chemiluminescence, and may also include fluorescence microscopy, light microscopy image analysis and video recording. Weaver et al. does not disclose using CTC to detect respiring bacteria.

Nader et al., U.S. Pat. No. 5,173,187 discloses that by means of immunofluorescence, bacteria in a mixture can be specifically labelled, and individual types of bacteria can be detected qualitatively under a fluorescence microscope, with an image analysis system and then quantitatively in a flow cytometer. Nader et al. does not disclose using CTC to detect respiring bacteria.

Melnicoff et al., U.S. Pat. No. 5,256,532 discloses methods, reagents and test kits for determining populations of biological entities. The patent discloses coupling of a detectable reporter substance nonselectively to the analyte which can be prokaryotic cells and later contacting the test sample with a specific binding substance which binds specifically to one characteristic determination of the analyte, and separating the components of the test sample and detecting the occurrence of the reporter substance in the sample. The reporter substance may be detected by fluorescence. In a preferred embodiment the nonselective reporter substance is linked to a lipid component of a biomembrane. Melnicoff et al. does not disclose using CTC to detect respiring bacteria.

Edberg et al., U.S. Pat. No. 4,925,789 discloses a method and medium for use in detecting target microbes in a tube from a sample of contaminated material. The testing method of Egberg et al. provides a selective growth medium for a target microbe and includes a specific nutrient which only the target microbe can metabolize. The specific nutrient is modified by attaching a sample altering moiety thereto, thereby converting the nutrient to a nutrient indicator. The sample altering moiety is activated to alter the sample only if the specific nutrient is metabolized by the target microbe. Edberg et al. does not disclose using CTC to detect respiring bacteria.

Waggoner et al. U.S. Pat. No. 5,268,486 is directed to a water soluble luminescent dye for use in immunoassays and which can be used for the detection of bacteria.

Rodriguez, et al., Use of a Fluorescent Redox Probe for Direct Visualization of Actively Respiring Bacteria, *Applied and Environmental Microbiology*, June 1992, Vol 58, pages 1801–1808 discloses that a redox probe 5-cyano-23-ditolyl tetrazolium chloride (CTC) may be employed for direct epifluorescent microscopic enumeration of respiring bacteria in environmental samples. Rodriguez discloses the use of dark membrane filters (black Nuclepore membranes) for microscopic visualization of respiring bacteria. Rodriguez et al. does not disclose a method including a step of determining specificity of the bacteria using immunofluorescence.

Schaule et al., "Use of 5-Cyano-2,3-Ditolyl tetrazolium Chloride (CTC) for Quantifying Plant Sessile Respiring Bacteria in Drinking Water", *Applied and Environmental Microbiology*, November 1993, pages 3850- 3857, Volume 59, Number 11, discloses that direct microscopic quantitation of respiring bacteria can be performed for drinking water samples using 5-Cyano-2,3-Ditolyl tetrazolium Chloride. Schaule et al. does not disclose a method including a step of determining specificity of the bacteria using immunofluorescence.

Chemical Abstracts Vol. 100 (1984) 188419*d* (U.S. Pat. No. 4,434,236 to Freytag) discloses a method of rapid detection of analytes in a sample. The sample is contacted with a solid phase having immobilized thereon an analyte analog to which there is displaceably bound a labeled anti-analyte antibody. The analyte may be a bacterium.

Chemical Abstracts Vol. 102 (1985) 42486*t* discloses a solid phase immunoassay for detecting bacteria. The immunoassay uses an immunoreactant attached to cells such as bacteria and a fluorescent or phosphorescent label.

However, prior art methods take a long time to conduct and do not simultaneously detect, identify and enumerate individual respiration of bacteria. The present method can be used to monitor the performance of water reclamation and storage systems. The present method may also be useful in tracing disease outbreaks, and in other public health situations such as water and wastewater treatment, storage and distribution. The method of the invention may also be used for routinely monitoring foods for quality control or grading purposes.

The present method overcomes the deficiencies of prior art methods by providing a rapid method for the detection, identification and enumeration of respiring microorganisms comprising the steps of a) passing a microbial sample through a collecting device to capture the cells;

b) adding to the collecting device a fluorochrome dye specific for the detection of respiring microbes and allowing the dye to incubate;

c) treating the collecting device with a reactive fluorescent antibody which reacts with a target microorganism of interest present in said microbial sample;

d) mounting said collecting device for examination by fluorescence microscopy in which a suitable light filter system is used to excite the fluorochrome dye and fluorescent antibody to fluoresce; and e) quantifying said respiring target microbial cells.

An advantage of the method of the present invention is that it is relatively rapid and minimizes actual labor input to about 1–2 hours with a total assay time of 3 to 6 hours. The procedure is amenable to automated examination using video image analysis technology.

DISCLOSURE OF THE INVENTION

It is thus an object of the present invention to provide a rapid method for the detection, identification and enumeration of respiring microorganisms.

It is a further object to provide a rapid method for testing potable water sources and water storage areas for microbial contaminants.

Additional objects of the invention will become apparent to one of skill in the art from the disclosure of the invention, below.

The present invention provides a rapid method for the detection, identification and enumeration of respiring bacteria and other microorganisms.

In a preferred embodiment the method comprises the steps of a) passing a microbial sample through a collecting device to capture the cells;

b) adding to the collecting device a fluorochrome dye specific for the detection of respiring microorganisms and allowing the dye to incubate;

c) treating the collecting device with a reactive fluorescent antibody which reacts with target cells of interest present in said microbial sample;

d) mounting the collecting device for examination by fluorescence microscopy in which a suitable light filter system is used to excite the fluorochrome dye and fluorescent antibody to fluoresce; and e) quantifying the respiring microbial cells.

Preferably the fluorochrome dye specific for the detection of respiring bacteria is taken up by respiring microorganisms and reduced to insoluble formazan crystals by the cytochrome system of said microbes. More preferably the fluorochrome dye specific for the detection of respiring cells is a tetrazolium compound. Most preferred is tetrazolium compound which is 5-Cyano-2,3-Ditolyl Tetrazolium Chloride (CTC).

Additionally the invention provides a rapid method for the detection, identification and enumeration of respiring target microorganisms comprising the steps of a) filtering a sample through a membrane filter to capture cells;

b) transferring the membrane filter to a pad comprising a fluorochrome dye specific for the detection of respiring microorganisms;

c) incubating said microbial sample with said fluorochrome dye;

d) treating the surface of the membrane filter with a reactive fluorochrome labeled antibody which reacts with a specific microbial species or strain of interest present in said sample;

e) mounting said membrane filter for examination by fluorescence microscopy in which a suitable light filter system is used to excite the fluorochrome dye and fluorochrome labeled antibody to fluoresce; and f) quantifying said respiring target microbial cells.

DESCRIPTION OF THE INVENTION

Rapid methods which indicate physiological activity in bacteria include 5-cyano-2,3-ditolyl tetrazolium chloride (CTC), a fluorescent analogue of iodonitro tetrazolium chloride (INT) which indicates respiratory activity (Roderiguez, G.G., D. Phipps, K. Ishiguro & H.F. Ridgway. 1992. Use of a fluorescent redox probe for direct visualization of actively respiring bacteria. Appl. Environ. Microbiol. 58:1801–1808). Rhodamine 123 is another fluorochrome which indicates proton motive force (Kaprelyants, A.S. & D.B. Kell. 1992. Rapid assessment of bacterial viability and vitality by rhodamine 123 and flow cytometry. J. Appl. Bacteriol. 72:410–422).

2-(p-iodophenyl)-3-(p-nitrophenyl)-5-phenyl tetrazolium Chloride (INT) has been used in ecological and environmental studies to indicate respiratory activity in bacteria (Zimmerman, R., R.M. Iturriaga, and J. Becker-Birck. 1978 Simultaneous determination of the total number of aquatic bacteria and the number thereof involved in respiration. Applied and Environmental Microbiology 36:926–935.) The INT acts as an artificial electron acceptor and is converted to insoluble red crystals of INT-formazan within the cells of metabolically active bacteria. Another compound, 5-cyano-2,3-ditolyl tetrazolium chloride (CTC) has been developed (Stellmach and Severin, German Patent DE 3418852 Al) which is similarly converted to CTC-formazan crystals which are fluorescent when examined by epifluorescent microscopy using appropriate excitation, barrier and emission filters. This method was used to assess the effects of disinfection of bacteria in biofilms (Yu, F.P., and G.A. McFeters. 1994 Rapid in situ assessment of physiological activities in bacterial biofilms using fluorescent probes. Journal of Microbiological Methods [in press]), and also adapted for use with bacteria collected in polycarbonate membrane filters.

In another approach, the direct viable count (DVC) method, cells are incubated for a few hours with appropriate nutrients and a quinoline antibiotic (usually nalidixic acid) which prevents division and hence causes viable (nutrient responsive) cells to elongate (Kogure, K., U. Simidu & N. Taga. 1979. A tentative direct microscopic method for counting living marine bacteria. Can. J.Microbiol. 25:415–420).

Respiring cells may also be enumerated by microcolony formation, where cells are immobilized on a polycarbonate membrane and incubated for a few hours on an appropriate medium which facilitates the development of microcolonies by nutrient responsive cells (Powell, E.O. 1956. A rapid method for determining the proportion of viable bacteria in a culture. J. Gen. Microbiol. 14:153–159; Postgate, J.R., J.E. Crumpton & J.R. Hunter. 1961. The measurement of bacterial viabilities by slide culture. J. Gen. Microbiol. 24:15–24).

CTC and rhodamine 123 were used for physiological assessment of biofilms following disinfection. (Yu, F.P., B. Pyle & G. McFeters. 1993. A direct viable count method for the enumeration of attached bacteria and assessment of biofilm disinfection, Journal of Microbiological Methods 17:167–180.) Rhodamine 123 and CTC have also been used in conjunction with flow cytometry (Diaper, J.P., K. Tither & C. Edwards. 1992. Rapid assessment of bacterial viability by flow cytometry. Appl. Microbiol. Biotechnol. 38:268–272; Kaprelyants, A.S. & D.B. Kell. 1992. Rapid assessment of bacterial viability and vitality by rhodamine 123 and flow cytometry. J. Appl. Bacteriol. 72:410–422; Kaprelyants, A.S. & D.B. Kell. 1993. The use of 5- cyano-2,3-ditolyl tetrazolium chloride and flow cytometry for the visualization of respiratory activity in individual cells of *Micrococus luteus*. J. Microbiol. Meth. 17:115–122), and CTC has been used to quantify planktonic and sessile bacteria in drinking water.

All of these methods are non-specific, i.e. although they may be used with pure cultures of specific organisms, they will not differentiate between bacterial species when applied to mixed populations.

On the other hand, methods for detecting specific bacteria, e.g. fluorescent antibodies or oligonucleotide probes, have not been developed to indicate physiological activity or viability of bacteria.

Microcolony formation has previously been combined with immunofluorescence for the detection of viable Listeria (Sheridan, J.J., I. Walls, J. McLaughlin, D. McDowell & R. Welch. 1991. Use of a microcolony technique combined with an indirect immunofluorescence test for the rapid detection of Listeria in raw meat. Lett. Appl. Microbiol. 13:140–144) and Salmonella (Roderigues, U.M. & R.G. Kroll. 1990. Rapid detection of salmonellas in raw meats using a fluorescent antibody-microcolony technique. J. Appl. Bacteriol. 68:213–223). The direct viable count method has also been successfully combined with immunofluorescence for the detection of viable *Vibrio cholerae* (Brayton, P.R. & R.R. Colwell. 1987. Fluorescent antibody staining method for enumeration of viable environmental *Vibrio cholerae* 01. J. Microbiol. Meth. 6:309–314), and *Escherichia coli* and *Salmonella enteritidis* (Roszak, D.B. &

R.R. Colwell. 1987. Metabolic activity of bacterial cells enumerated by direct viable count. Appl. Environ. Microbiol. 53:2889–2983).

While the polymerase chain reaction has been widely employed for detection of natural bacterial populations in water (e.g. Bej, E.K., J.L. DiCesare, L. Haff, & R.M. Atlas. 1991. Detection of *Escherichia coli* and Shigella spp. in water by using a polymerase chain reaction and gene probes Appl. Environ. Microbiol. 57:1013–1017), the procedure is tedious and lengthy, requiring specialized thermal cycling equipment. Furthermore, no PCR method has been proposed for the reliable detection, enumeration and examination of individual viable cells. Oligonucleotide probes have been developed for a wide range of bacteria (Ward, D.M., M.M. Bateson, R. Weller & A.L. Ruff-Roberts. 1992. Ribosomal RNA analysis of microorganisms as they occur in nature. In *Advances in Microbial Ecology*, Vol. 12, K.C. Marshall (ed.), pp. 219–286. New York, Plenum Press), and fluorescent 16s rRNA oligonucleotide probes have been investigated using an *E. coli* 16s rRNA sequence and two bacterial sequences in conjunction with DAPI for total direct counts in water samples (Hicks, R.E., R.I. Amann & D.A. Stahl. 1992. Dual staining of natural bacterioplankton with 4', 6-diamidino-2-phenylindole and fluorescent oligonucleotide probes targeting kingdom-level 16S rRNA sequences. Appl. Environ. Microbiol. 58:2158–2163). Similarly, single bacterial cells have been identified using digoxigenin-labeled rRNA probes (Zarda, B., R. Amann, G. Wallner & K.-H. Schleifer. 1991. Identification of single bacterial cells using digoxigenin-labelled, rRNA-targeted oligonucleotides. J. Gen. Microbiol. 137:2823–2830), and fluorescently labeled oligonucleotide probes have been used for detection of microorganisms in soil (Hahn, D., R.I. Amann, W. Ludwig, A.D.L. Akkermans & K.-H. Schleifer. 1992 Detection of micro-organisms in soil after in situ hybridization with rRNA-targeted, fluorescently labelled oligonucleotides. J. Gen. Microbiol. 138:879–887). Direct microscopic examination was employed following staining with DAPI, gel transfer, and hybridization with rhodamine-labeled probes. Although these techniques are rapid and specific, they are of little value in establishing respiration of bacteria and viability.

The present method involves the treatment and incubation of cells concentrated by a collecting device, such as a filter membrane, followed by microscopic examination to determine viability, respiration, quantification and identity of the microorganism. Physiological assessment is based on the reaction of fluorogenic substrates which permit the evaluation of the respiratory activity of the microorganism. The identification is performed with labeled antibodies or oligonucleotide probes.

Figure 1:
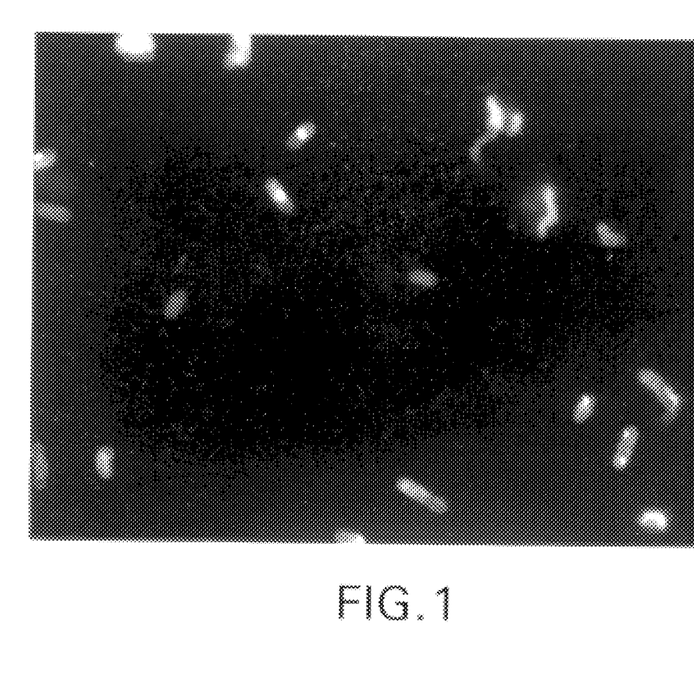
FIG. 1 shows a photomicrograph of cells of *Escherichia coli* 0157:H7 reacted with rabbit anti-0157 primary antiserum and with goat anti-rabbit fluorescein conjugate after incubation with CTC. Cells stained green have reacted with the fluorescein-labelled antibody. Those cells with an orange-yellow spot in them have reduced CTC to CTC formazan which indicates respiratory activity.
Figure 2:
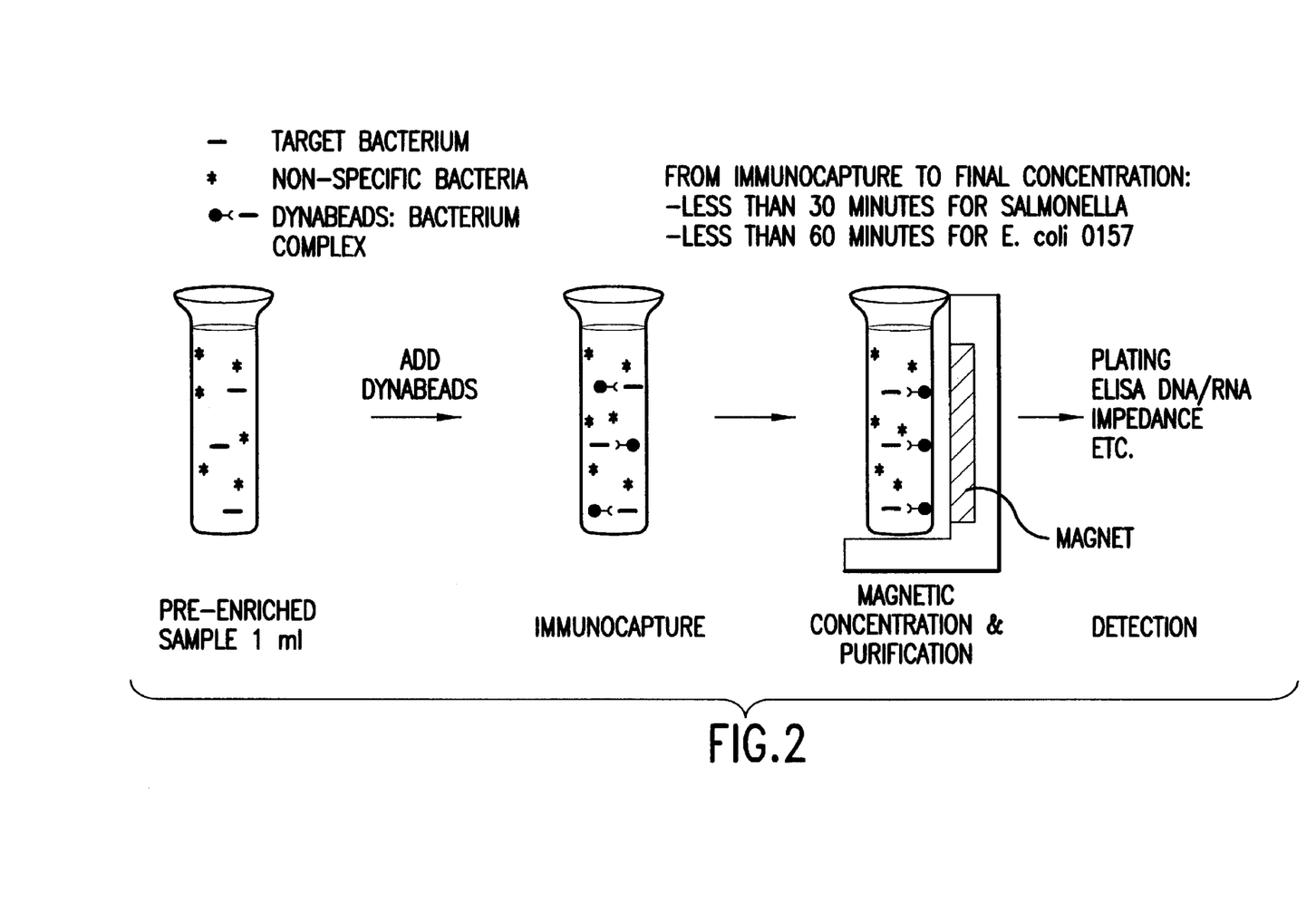
FIG. 2 shows a schematic diagram of the use of magnetic beads in the method of the invention.

Research on microscopic methods for the detection of bacteria in spacecraft water systems has led us to develop a method in which the CTC incubation is combined with a fluorescent antibody test (FIG. 1). The method has been performed successfully with, for example, *E. coli* 0157:H7 and *Salmonella typhimurium*. The method can be performed with any microorganism which can take up and metabolize CTC by respiratory cytochrome activity.

Briefly, cells in a liquid sample are collected on the surface of a 0.2 μm porosity polycarbonate filter membrane. The membrane is incubated at room temperature on a pad which is saturated with a buffer solution containing CTC. After 1–3 hours incubation, the membrane is fixed with formalin and heated. A drop of primary antibody which is specific for the target organism is applied and incubated for 20–30 min, followed by rinsing with buffer to remove unbound antibody. A drop of secondary fluorescent antibody conjugate which is specific for the primary antibody is applied and incubated for 20–30 min. The membrane is rinsed and mounted in buffered glycerol for examination by epifluorescence microscopy. Using appropriate excitation/barrier/emission light filters, cells which have accumulated CTC-formazan crystals contain yellow/red spots, and those which have reacted with the fluorescein-conjugated antibody appear green (FIG. 1).

The following is an example of the method according to the present invention.

EXAMPLE 1

A liquid sample containing bacteria is filtered through a membrane (black polycarbonate) to capture bacteria from the sample.

The membrane is transferred to a pad which is saturated with a medium containing a fluorochrome (5-Cyano-2,3-Ditolyl tetrazolium Chloride (CTC)) which indicates the viability of a cell when the fluorochrome is taken up and metabolized.

After incubation with a fluorochrome, the surface of the membrane filter is treated with a particular antibody which will react with the target bacteria. After reaction with the antibody, the membrane filter is rinsed to remove unbound antibody. The reactive antibody and fluorescent CTC formazan are then visualized.

In a preferred embodiment a gel blocking step may be used to suppress background hybridization in the fluorescent antibody labelling step of the method of the invention. To perform this step, one drop of hydrolyzed gelatin solution is gently spread over the membrane filter surface or collection device surface. The membrane is brought to near dryness. Gelatin is prepared by autoclaving a 2% gelatin solution at pH 10 followed by adjustment to Ph 7.2 and freezing in 1 ml aliquots. Prior to use, the hydrolyzed gelatin is diluted with distilled water and filter sterilized. (Cochran-Stafira, D.L. & M. Starzyk. 1989. Membrane filter fluorescent antibody technique for the detection and enumeration of the genus Thermus in water. Microbios 60:159–165.) One drop of filter sterilized FITC-conjugated antibody, appropriately diluted with phosphate buffered saline, is added to the gel coated membrane. At the end of incubation the membrane filter is mounted for bacterial identification and quantification.

The membrane filter is examined by fluorescence microscopy in which a suitable light filter system is used to excite the viability and antibody-conjugated fluorochrome to fluorescence.

The bacteria may then be quantified by taking into account the original volume of the liquid filtered, the filtration area and the microscopic field area including the number of fields examined.

Table 1 provides a second example of the method of the present invention.

TABLE 1

Procedure for detection of cells which reduce CTC and react to a specific fluorescent antibody, using polycarbonate membrane.

Pass sample or diluted culture through a 0.2 μm porosity black polycarbonate membrane to obtain 10–100 cells in a microscope field
↓
Transfer membrane to a pad saturated with medium containing CTC and incubate at room temperature
↓
Fix by lifting the membrane and adding 0.1 ml 37% formalin to the pad, replacing the membrane and incubating at least 5 min
↓
Place membrane in glass petri dish, heat for 10 min at ca. 65° C.
↓
Place a drop of gelatin solution on membrane, spread, heat at ca. 55° C. until almost dry; allow to dry and cool at room temperature
↓
Place a drop of diluted antiserum on the membrane, spread, and incubate in an enclosed petri dish for 30 min at room temperature
↓
Transfer membrane to filter funnel apparatus, wash with two 0.5 ml volumes of PBS
↓
Replace membrane in petri dish, place a drop of fluorescent conjugated anti-antiserum on the membrane, spread and incubate in closed dish for 30 min at room temperature
↓
Transfer membrane to filter funnel apparatus, wash with three 0.5 ml volumes of PBS
↓
Mount filter in buffered glycerol, add coverslip and examine with epifluorescence using 100% objective under oil immersion; use light filters appropriate for the fluorochrome which was conjugated to the anti-antiserum.

An advantage of the present method is that it is relatively rapid and minimizes actual labor input to about 1 to 2 hours with a total assay time of 3 to 6 hours. Several samples can be processed at the same time. The procedure is amenable to automated examination using video image analysis technology. The method provides for the rapid detection, identification and enumeration of respiring bacteria.

In the alternative, incubation of CTC can be performed by spraying or liquid application onto the surface of a membrane. Similarly antibodies or probes can be applied by other means known to those of skill in the relevant art. In an alternative embodiment, the collecting device to capture the bacteria from a contaminated sample comprises a centrifuge for performing sedimentation field flow fractionation. The method of sedimentation field-flow fractionation is known to those of skill in the art (see Sharma et al., "Physical Characterization and Quantification of Bacteria by Sedimentation Field-Flow Fractionation", *Applied and Experimental Microbiology*, Vol. 59, No. 6, June 1993, pp 1864–1875, "incorporated herein by reference in its entirety")."

EXAMPLE 2

Incubation for CTC reduction, cell elongation or microcolony formation was performed, followed by fluorescent antibody (FAb) reaction or nucleic acid hybridization directly on polycarbonate filter membranes. Both fluorescent antibody techniques (Cochran-Stafira, D.L. & M.J. Starzyk. Membrane-filter fluorescent antibody technique for the detection and enumeration of the genus Thermus in water. Microbios 60:159–165; Desmonts, C., J. Minet, R. Colwell & M. Cormier. 1990. Fluorescent-antibody method useful for detecting viable but nonculturable Salmonella spp. in chlorinated wastewater. Appl. Environ. Microbiol. 56:1448–1452 and oligonucleotide probe methods (Heidelberg, J.F., K.R. O'Niel, D. Jacobs & R.R. Colwell. 1993. Enumeration of *Vibrio vulnificus* on membrane filters with a fluorescently labeled oligonucleotide probe specific for kingdom-level 16S rRNA sequences. Appl. Environ. Microbiol. 59:3464–3476) have been performed directly on filter membranes.

A protocol we have developed for the CTC/Fab approach is shown in Table 1. Aphotomicrograph (FIG. 1) indicates the visual appearance of a typical sample prepared by the protocol outlined in Table 1.

The viability/nucleotide probe method is based on initial incubation for microcolony formation. Cells which respond by growing into microcolonies will have increased rRNA content and because there will be several cells they will be more easily detected.

Automation and electronic data capture and processing are desirable in the context of water quality monitoring in the spacecraft environment. We have previously developed methods for rapid enumeration of viable bacteria by image analysis (Singh, A., B.H. Pyle & G.A. McFeters. 1989. Rapid enumeration of bacteria by image analysis epifluorescence microscopy. J. Microbiol. Meth. 10:91–102; Singh, A. F.P. Yu & G.A. McFeters. 1990. Rapid detection of chlorine-induced injury by the direct viable count method using image analysis. Appl. Environ. Microbiol. 56:389–394). These procedures were based on the direct viable count technique (Kogure, K., U. Simidu & N. Taga. 1979. A tentative direct microscopic method for counting living marine bacteria. Can. J. Microbiol. 25:415–420). The combined methods of the present invention are also amenable to quantification by image analysis.

In an alternative embodiment, the invention provides for a method for the detection, identification and enumeration of a respiring target bacterium comprising the steps of a) mixing immunomagnetic beads comprising an antibody which specifically binds to a target bacteria with a liquid sample comprising said target bacteria;

b) allowing said liquid sample to interact with the beads for up to an hour;

c) placing the sample in a magnetic separator which causes the magnetic beads to which target bacteria have attached to separate from the liquid sample;

d) aspirating the liquid from the liquid sample, leaving the beads with bacteria attached;

e) washing the beads with a solution which removes loosely bound bacteria and other particles from the liquid sample;

f) mixing beads with bacteria attached with a fluorochrome dye specific for the detection of respiring bacteria;

g) treating bacteria on the beads with a fluorescent stain or a specific fluorescent conjugated antibody;

h) mounting said sample for examination by epifluorescent microscopy, in which a suitable light filter system is used to excite the fluorochrome dye and fluorochrome labeled antibody to fluoresce; and i) quantifying said respiring target bacteria.

Again it is preferred that the fluorochrome dye specific for the detection of respiring bacteria is taken up by respiring bacteria and reduced to insoluble formazan crystals by the cytochrome system of the bacteria, such as 5-Cyano-2,3-Ditolyl Tetrazolium Chloride (CTC).

Materials are commercially available which can facilitate concentration and separation of target bacteria from food homogenates. The technique is known as immunomagnetic separation (IMS).

Immunological separation of bacteria from food samples using specific antibodies coated on a variety of surfaces has led to the use of magnetizable particles (Blackburn, C. de W. 1993 Rapid and alternative methods for the detection of salmonellas in foods. Journal of Applied Bacteriology 75:199–214). IMS techniques utilize small particles or beads coated with antibodies against surface antigens of specific bacteria (Olsvik, O., T. Popvic, E. Skjerve, K.S. Cudjoe, E. Hornes, J. Ugelstad, and M. Uhlen. 1994 Magnetic separation techniques in diagnostic microbiology. Clinical Microbiology Reviews 7:43–54). The super-paramagnetic beads become magnetic when in a magnetic field but become nonmagnetic as soon as the field is removed. Thus, the particles remain in suspension when they are not in a magnetic field, and can be readily concentrated by applying a magnetic field. Isolation of specific bacteria bound to beads has usually been accomplished by cultivation of captured cells in broth or on solid media. Bacteria bound to magnetic beads remain viable when provided with adequate nutrients.

IMS has been used to isolate a variety of bacteria including *E. coli* K88 (Lund, A., A.L. Hellemann, and F. Vartdal. 1988 Rapid isolation of K88$^+$ *Escherichia coli* by using immunomagnetic particles. Journal of Clinical Microbiology 26:2572–2575), *Salmonella* spp. (Blackburn and Patel, 1989; Skjerve and Olsvik, 1991), *Listeria monocytogenes* (Skjerbe et al., 1990), and *Vibrio parahaemolyticus* serotype K (Tomoyasu, T. 1992 Development of the immunomagnetic enrichment method selective for *Vibrio parahaemolyticus* serotype K and its application to food poisoning study. Applied and Environmental Microbiology 58:2679–2682). *Shigella dysenteriae* and *S. flexneri* in feces were detected by immunomagnetic assay with monoclonal antibodies (Islam, D., S. Tzipori, M. Islam, and A.A. Lindberg. 1993 Rapid detection of *Shigella dysenteriae* and *Shigella flexneri* in feces by an immunomagnetic assay with monoclonal antibodies. European Journal of Clinical Microbiology and Infectious Diseases 12:25–32). Okrend et al. (Okrend, A.J.G., B.E. Rose, and C.P. Lattuada. 1992 Isolation of *Escherichia coli* 0157:H7 using 0157 specific antibody coated magnetic beads. Journal of Food Protection 55:214–217) found that *E. coli* 0157:H7 could be sensitively and specifically concentrated from ground beef by using magnetic beads coated with 0157 antibody. The cells were subsequently cultivated in a nonselective growth medium. *E. coli* 0157:H7 strains have also been extracted from enrichment broths (Fratamico, P.M., F.J. Schultz, and R.L. Buchanan. 1992 Rapid isolation of *Escherichia coli* 0157:H7 from enrichment cultures of foods using an immunomagnetic separation method. Food Microbiology 9:105–113). The number of *E. coli* 0157 recovered was related to the number of *E. coli* 0157 in the sample. The sensitivity of recovery of *E. coli* 0157:H7 was 10 CFU/ml in the enrichment medium. It was demonstrated that *E. coli* 0157:H7 cells attached to the beads could be visualized by incubation with FITC labeled polyclonal antiserum against *E. coli* 0157:H7 for 30 min followed by epifluorescent microscopic examination.

Magnetic beads may be obtained commercially (e.g. Dynal, New York), and these may be supplied coated with the *E. coli* 0157 antibody.

Essentially, *E. coli* 0157:H7 bacteria in hamburger meat can be concentrated by immunomagnetic capture, as has been done with salmonellae (Vermunt, A.E.M., A.A.J.M. Franken, and R.R. Beumer. 1992 Isolation of salmonellas by immunomagnetic separation. Journal of Applied Bacteriology 72:112–118). After separation of the beads (with bacteria attached) from the meat suspension, the bead/cell particles are trapped on a filter membrane. The membrane is incubated for a few hours with a tetrazolium compound which, when taken up into respiring cells is reduced to a fluorescent formazan crystal. Reaction of the cells with a contrasting fluorescent antibody permits the *E. coli* cells to be specifically labelled by the fluorescent dye. Subsequent direct microscopic observation and enumeration of the sample on the membrane filter permits discrimination of cells which were both metabolically active and of the specific 0157:H7 antigenic type.

An important feature of the method of the invention is that it will discriminate between viable respiring bacteria which are possibly infectious and non-respiring cells which would have little likelihood of causing infections.

The proposed method has a number of advantages over other techniques, including:

The immunomagnetic capture step permits not only cell concentration, but also the selection of a specific antigenic cell type. Use of the *E. coli* 0157 antigen concentrates bacteria that are likely to produce illness while eliminating other bacterial species from the bead concentrate.

The short term incubation with the respiratory fluorochrome provides rapid evaluation of the physiological status of the cells captured, indicating the potential for proliferation of the pathogen in a stored food product and its ability to infect consumers.

Reaction with a second fluorescently labelled antibody provides confirmation that the bacteria selected were indeed the target pathogen. For example, *E. coli* 0157 antibodies different from the primary capture 0157 antibody, e.g. from another manufacturer, will confirm the presence of *E. coli* 0157. Alternatively, a different antigen can be used for the confirmation, such as the H7 flagellar antigen or a fimbrial antigen. A similar approach can be taken when a pathogen other than *E. coli* 0157 is the target organism.

Epifluorescence microscopic examination allows the enumeration of individual viable cells of *E. coli* 0157, in contrast to cultivation and enrichment techniques in which each colony may be formed by more than one cell.

The time required to complete the immunomagnetic concentration, viability incubation, fluorescent antibody reaction and microscopic examination is approximately 4–6 h. The procedure can be automated at several steps, reducing the time required to as little as three hours. These time requirements reflect a truly rapid method, allowing meat samples to be briefly withheld until results of the test become available.

For the simple, rapid detection of *E. coli* 0157:H7 in ground beef, meat samples are added to a suitable extraction medium, e.g. sterile physiological saline containing 5 mg/ml (final concentration) of Protamine (Okrend, A.J.G., B.E. Rose, and C.P. Lattuada. 1992 Isolation of *Escherichia coli* 0157:H7 using 0157 specific antibody coated magnetic beads. Journal of Food Protection 55:214–217). Following brief (5–10 min) processing in a Stomacher, the homogenate is transferred to a tube and a suspension of anti-*E. coli* 0157 0.28 μm diameter Dynabeads (Dynal, N.Y.) added. The suspension is incubated with the beads for 10–60 min, then placed in a magnetic particle concentrator (Dynal) to immobilize the beads and captured cells.

After 1–5 min, the liquid meat/buffer suspension is removed by aspiration. The tube is taken off the magnetic separator and the beads resuspended in fresh buffer and washed. The CTC incubation can be carried out either directly with the bead/cell suspension or after collection of the bead/cell particles on a polycarbonate filter membrane. Filtration can prevent the loss of target cells during subsequent manipulations. This is followed by incubation with fluorescently-labelled E. coli 0157 antibody, rinsing and mounting for epifluorescent microscopic examination and counting.

The number of fluorescent antibody positive bacterial cells which contain CTC-formazan crystals is counted as the number of viable E. coli 0157 cells recovered. Non-viable cells (CTC-negative) are also counted to permit quantification of the total number of E. coli 0157 in the meat sample.

Variations of the technique include the use of alternative, and possibly multiple, confirmatory fluorescent antibodies. Alternatives include antibodies for the E. coli H7 flagellar antigen, or a fimbrial antigen (Levine, M.M. 1987 *Escherichia coli that cause diarrhea: enterotoxigenic, enteropathogenic, enteroinvasive, enterohemorrhagic, and enteroadherent.* Journal of Infectious Diseases 155:377–39).

Different homogenization buffers can be used to obtain optimal immunomagnetic recovery of bacteria. Other than physiological saline containing protamine (Okrend, A.J.G., B.E. Rose, and C.P. Lattuada. 1992 Isolation of *Escherichia coli* 0157:H7 using 0157 specific antibody coated magnetic beads. Journal of Food Protection 55:214–217), plain physiological saline without Protamine may be used. Other possibilities include phosphate buffered saline (Doyle, M.P. and J.L. Schoeni. 1987 Isolation of *Escherichia coli* 0157:H7 from retail fresh meat and poultry. Applied and Environmental Microbiology 53:2394–2396 and Lund, A., A.L. Hellemann, and F. Vartdal. 1988 Rapid isolation of K88+ *Escherichia coli* by using immunomagnetic particles. Journal of Clinical Microbiology 26:2572–2575) with and without Protamine, and phosphate-buffered peptone water with 0.05% Tween 20 (Skjerve, E., and O. Olsvik. 1991 Immunomagnetic separation of Salmonella from foods. International Journal of Food Microbiology 14:11–18) or with 5 mg/ml protamine substituted for the Tween 20.

The attachment procedure may be varied. One minute vortexing and 10 min stationary incubation followed by vortexing (Okrend, A.J.G., B.E. Rose, and C.P. Lattuada. 1992 Isolation of *Escherichia coli* 0157:H7 using 0157 specific antibody coated magnetic beads. Journal of Food Protection 55:214–217) may be used. Room temperature incubation with shaking for 10 min (Vermunt, A.E.M., A.A.J.M. Franken, and R.R. Beumer. 1992 Isolation of salmonellas by immunomagnetic separation. Journal of Applied Bacteriology 72:112–118) or with rotation for 15 or 60 min (Fratamico, P.M., F.J. Schultz, and R.L. Buchanan. 1992 Rapid isolation of *Escherichia coli* 0157:H7 from enrichment cultures of foods using an immunomagnetic separation method. Food Microbiology 9:105–113) may also be used.

Direct CTC incubation of cells on beads in suspension or incubation following filtration can be used. Different membrane filters, e.g. Millipore or Nuclepore black polycarbonate membranes can be used in the present method for the filtration treatments.

CTC incubation media containing phosphate, e.g. R2A (Reasoner, D.J., and E.E. Geldreich. 1985 A new medium for the enumeration and subculture of bacteria from potable water. Applied and Environmental Microbiology 49:1–7) broth, can inhibit CTC reduction. Physiological saline can be used as a medium or a mixture of casamino acids (0.3%) and yeast extract (0.03%) (Singh, A., B. Pyle, and G. McFeters. 1989 Rapid enumeration of viable bacteria by image analysis. Journal of Microbiological Methods 10:91–101). Other more appropriate formulations may be obvious to one skilled in the art.

The CTC concentration may be varied over the range 1–5 mM. The preferred concentration for optimal reduction usually occurs in the range 2–5 mM.

The application of multiple confirmatory fluorescent antibodies, and direct vs. indirect fluorescent antibody techniques can be used. When multiple fluorescent antibodies are used, they are conjugated with contrasting fluorescent compounds. The epifluorescent excitation/barrier/emission filter combinations may also be varied in the present method as is understood by those of skill in the art.

Incubation with CTC to detect respiratis activity is compatible with immunomagnetic capture and subsequent fluorescent antibody confirmation. The proposed method does not involve a cultivation step, and it is expected that there will be a reasonable correlation with conventional culture methods. Optimization of the procedures should enable detection of very low numbers of target bacteria in ground beef.

While detection of less than 1 colony forming unit per gram of meat is expected, it has been found that levels of 10–6200 individual E. coli 0157:H7 per gram have been detected in beef samples associated with foodborne illness (Todd et al, 1988). Thus, a rapid, specific method which can detect 10 viable E. coli 0157 per gram sample would be useful in the identification of meats which were likely to cause food-borne disease.

The specificity of E. coli 0157:H7 antigens is debated. The advantage of the present method is that two antigens can be used, one for the initial capture of the target bacteria on the immunomagnetic beads, and the other for confirmation after the incubation for respiratory activity. Thus, if a broad-spectrum antibody which may cross-react with some other species is used as the immunomagnetic bead antibody, this would help to optimize detection. A more specific fluorescent antibody can then be used for confirmation.

The proposed procedure, as outlined above, could be modified at several points to enhance its potential application. For example, as new specific antibodies become available, they could be used for the immunomagnetic separation step. If an antibody were available which would detect a wide range of verotoxigenic E. coli, including 0157:H7, this would provide a more realizable assessment of the presence of enterohemorrhagic pathogens (Milley and Sekla, 1992).

The methods described above can also be modified for the detection of, for example, the pathogenic bacterium *Legionella pneumophila* which has been detected by immunofluorescence (Edelstein, P.H. 1993. Laboratory diagnosis of Legionnaires Disease: an update from 1984. In Legionella current Status and Merging Perspectives, Barbaree, J.M., Breiman, F.R., and Dufour, A.P. (Eds.), American Society for Microbiology, Washington, 7–11; Verissimo et al. 1991. Distribution of Legionella spp. in hydrothermal areas in continental Portugal and the Island of Sao Miguel, Azores. *Applied and Environmental Microbiology* 57:2921–2927).

The fluorescent tetrazolium compound CTC was originally used to detect respiratory activity in eukaryotic cells (Severin, Stellmach and Nachtigal. 1985. Fluorimetric assay of redox activity in cells. *Analytica Chimica Acta* 170:341–346), and similar respiratory systems exist in protozoan species which are also eukaryotes (Sleigh, M.A. 1991) The nature of protozoa. In Parasitic Protozoa, Second Edition, Volume 1, Kreier, J.P. and Baker, J.R. (Eds.), Academic Press, Inc., San Diego, P. 13). Immunofluorescent methods for detection and enumeration of the parasitic microbial protozoan species Cryptosporidium and Giardia (Rose et al. 1989. Evaluation of immunofluorescence techniques for detection of *Cryptosporidium oocysts* and Giardia cysts from environmental samples. *Applied and Environmental Microbiology* 55:3189–3196) can be combined with fluorescent indicators of cell activity such as CTC as described above for bacterial species.

Fluorescent probes, other than CTC, which assay cellular physiological activity can be used. These include Rhodamine 123, which provides an estimation of transmembrane potential, or fluorescein diacetate which indicates esterase activity. These fluorochromes and others are discussed by McFeters et al (McFeters, G.A., Yu, F.P., Pyle, B.H., and Stewart, P.S. 1994 A minireview: Physiological assessment of bacteria using fluorochromes. *J. Microbiol. Meth.* [In Press]), and Rhodamine 123 has been applied successfully to the study of bacterial biofilms in our laboratory.

The confirmatory step with staining for microscopic examination can also be varied. For a rapid confirmation that cells have bound to the immunomagnetic particles, the rinsed particles can be stained with a general fluorochrome such as acridine orange or DAPI (McFeters et al., 1994). DAPI can be used in the same way as a counterstain after incubation with CTC. It is possible to follow the physiological activity incubation by treatment with a fluorescently labelled oligonucleotide probe with specificity for 16s rRNA of the target species. Many Gram-negative and some Gram-positive bacteria have been detected using fluorescent oligonucleotide probes (Amann, R., Ludwig, W., and Schleifer, K.-H. 1992 Identification and in situ detection of individual bacterial cells. *FEMS Microbiol. Lett.* 100:45–50). Probes for gene sequences which probe for Verotoxin or other toxins or specific cell constituents permit more specific conformation than that provided by fluorescent antibody techniques.

In an alternative embodiment, immunomagnetic beads with cells attached may be immobilized and incubated on a nutrient medium for a few hours to allow the attached target cells to form microcolonies. This pretreatment may be followed by visualization by immunofluorescence or fluorescent oligonucleotide probing, or by CTC incubation with either immunofluorescence or fluorescent oligonucleotide probe analysis.

EXAMPLE 3

In a preferred embodiment immunomagnetic beads which are coated with an antibody which specifically binds to a particular species of target bacteria are mixed with a liquid suspension which may contain the target bacteria. The sample suspension containing the beads is allowed to interact for up to an hour, with gentle agitation.

The tube containing the sample is placed in a magnetic separator which causes the magnetic beads to which target bacterial cells have attached to separate from the liquid suspension. The liquid suspension is aspirated out of the tube, leaving the beads with attached bacteria. The beads may be washed with appropriate solutions to remove loosely bound bacteria and other particles from the suspension.

The bacteria on the beads are mixed with a solution containing a tetrazolium compound which is taken up by respiring bacteria and reduced to insoluble formazan crystals by the cytochrome system. Following or simultaneous with incubation with the respiratory indicator, cells on the beads may be treated with a fluorescent stain or a specific fluorescent conjugated antibody. Specific fluorescent conjugated antibodies for target bacteria are known to those of skill in the art. (Bohlool, B.B. & E. Schmidt. 1980. The immunofluorescence approach in microbial ecology. pp. 203–241 In Advances in Microbial Ecology, Volume 4, edited by M. Alexander (Plenum Press, New York)).

The specimen is then mounted for examination by epifluorescent microscopy. When appropriate excitation/barrier/emission light filters are used, the formazan crystals fluoresce bright yellow/red in contrast with the fluorescent counterstain or immunofluorescent antibody. The cells may be enumerated and the number used to determine the number of respiring target cells in the original sample.

The method is applicable to the detection of respiring, viable bacteria of a particular target species in suspensions of food and in water, wastewater or sediment samples.

An advantage of the method lies in the combination of determining respiratory activity in conjunction with immunomagnetic capture and subsequent staining or fluorescent antibody confirmation. The immunomagnetic concentration step may be combined with membrane filtration to collect the beads and bacteria, thus precluding subsequent loss of bacteria from the beads during the respiratory incubation and final stainingsteps. Results would be obtained within 4–6 hours with limited labor input.

By means of immunofluorescence, bacteria in a mixture can be specifically labelled and thus individual types of bacteria can be detected qualitatively under a fluorescence microscope, also quantitatively with an image analysis system and then quantitatively in a flow cytometer.

For the determination by means of immunofluorescence, specific antibodies against the bacterial strains to be detected are produced and coupled to a fluorescence colored material. After incubation of the bacterial mixed culture with these antibodies, only the appropriate target bacteria of interest are fluorescently colored and can be detected under a fluorescence microscope.

The production of polyclonal or monoclonal antibodies which are needed for this technique takes place according to known processes which do not need to be further explained here. In principle, bacteria from a pure culture are killed, injected into an experimental animal (rabbit or mouse) and the antiserum is obtained therefrom or B-lymphocytes are isolated therefrom and used for the hybridoma technique.

Antibodies are selected on the basis of their specificity and utility as known to those of skill in the art. In the case where monoclonal antibodies have considerable cross-reactivities, this may be problematic for environmental samples and polyclonal antibodies may be used.

It is preferred that the magnetic beads used in the above method be Dynabeads®. Dynabeads® are uniform, superparamagnetic microspheres (2.8 microns in diameter) with affinity purified antibodies on their surface. When incubated with a sample, Dynabeads® will bind their target bacterium forming a bacterium:magnetic bead complex. This complex is separated from the heterogenous sample by placing the sample tube in a magnetic holder (Dynal MPC®). For example, Microbiology Selective Enrichment Products Dynabeads®, anti-*E.coli* 0157 Dynabeads®, anti-Salmonella, are designed for rapid, immunomagnetic selective enrichment of microorganisms directly from pre-enrichment broths.

The beads are rapid and simple to use, the protocol saves 24 hours of valuable testing time compared to conventional selective enrichment media. The beads have high sensitivity and will detect as low as 100 organisms/ml of pre-enriched sample. The beads allow for complete detection of over 200 serotypes of Salmonella and both motile and non-motile strains of E.coli 0157. An antibody coating of different specificity could be used to capture other specific target bacteria. The beads are also efficient providing concentration and purification of the sample by immunomagnetic separation (IMS) improves bacterial isolations.

The beads are versatile and can be used for many different sample types. For example, the beads are convenient in that hand-held instrumentation provides convenience and ease of use. Only a magnet (Dynal MPC®) is required for separation of the beads. Magnetic beads are flexible and can be conveniently combined with existing manual and automated detection methods (ELISA, PCR, and Impedance) for greater testing efficiency. The isolated and concentrated bacterium:bead complex can then be cultured on any selective culture medium or used in other detection systems. Dynabeadso® anti-E. coli 0157 are coated with affinity purified polyclonal anti-E. coli 0157 antibodies. Dynabeads® anti-Salmonella are coated with affinity purified polyclonal and monoclonal anti-Salmonella antibodies. Beads can be coated with other antibodies by the suppliers or in the testing laboratory.

The method of the present invention can be used to obtain a viable enumeration of biological entities with a cytochrome system. It is preferred to use the present method to enumerate bacteria or protozoa.

Representative suitable means for measuring biological material, using naturally occurring properties of biological entities, or using stains, includes physical means such as optical, weighing, sedimentation, field flow sedimentation fractionation, acoustic, magnetic, electrical and thermal means. It is preferred to use optical measurements wherein biological material volumes are measured using optical phenomenon such as light scattering, light absorbance or calorimetric, fluorescence, time-delayed fluorescence, phosphorescence and chemiluminescence.

Optical measurements can be often enhanced by treating or exposing bacteria to at least one staining process, wherein at least one stain is utilized to enhance the measurement of biological material.

Representative suitable types of stains which may be used in addition to the fluorochrome for the detection of respiring bacteria, include stains indicative of biological composition, stains indicative of enzyme activity, and stains indicative of cell membrane integrity. Such stains are generally selected to have readily measurable properties such as fluorescent stains, light absorbance stains and light scattering stains, and can be further selected according to the class of biological material which is stained, including, therefore, stains such as nucleic acid stains, protein stains, lipid stains, cell membrane stains, cell wall stains, stains responsive to enzyme activity, stains responsive to transmembrane potentials and cell surface receptor stains.

It is also useful to practice the present method with optical measurements made using apparatus such as flow cytometry apparatus, flow-through-microfluorimetry apparatus, optical particle analysis apparatus, fluorescence microscopy apparatus, light microscopy apparatus, image analysis apparatus and video recording apparatus.

Electrical measurements also have significant advantages, as electrical signals can be coupled directly to computational means. Thus, it is useful to practice this invention by employing electrical measurement means to measure biological material. Electrical measurements useful with bacteria include those involving electrical resistance particle analysis apparatus and dielectric property measurement apparatus and a dielectric property measurement apparatus.

For example, it is well established that a resistive cell counter, often termed a Coulter Counter, can use electrical resistance measurement to determine cell volume (see, for example, Kachel in Flow Cytometry and Sorting, Melamed et al (Eds), Wiley, N.Y., pp. 61–104).

In the case of bacterial cells stained by fluorescent compounds, optical analysis such as digital fluorescence microscopy or flow cytometry is used to analyze individual bacteria, using a wavelength band sufficiently different from that used for any detection or measurement of bacterial properties so that simultaneous, or serial, measurement of bacterial properties is possible. The associated fluorescence signals are acquired and analyzed, with correction for spectral overlap if necessary, by conventional means.

The magnitude of the optical signal due to the cell stain in each bacterium, or small group of bacteria, is compared to the fluorescence of individual cells, thereby providing a calibration. Comparison of the bacterial signal magnitude to that of individual cells provides the basis for determination of growth of individual cells, for which the growth determination can often be made within about one generation time, but without a need for significant prior culture to obtain large numbers of cells, and growth can also be determined over several generations, if desired.

By making a large number of such individual cell growth determinations, the distribution of growth rate, distribution of lag time, and the plating efficiency caused by the exposure to one or more compounds or agents can be automatically determined by computer calculation. Other measurements relating to cell survival and cell death, particularly vital stains such as transmembrane potential stains, membrane exclusion stains and intracellular enzyme activity responsive stains, can also be used. Manual or visual inspection and scoring of bacteria can also be used, but is relatively labor intensive and therefore more prone to error. Thus, the preferred process is that conducted using the automated measurement means.

This invention can be used to provide measurement of certain types of biological entities or bacteria, herein referred to as analyte entities, capable of reacting with and binding two or more labeled specific binding molecules, wherein the labeled specific binding molecules are measured directly by measuring one or more labels which have been attached to the individual labeled specific binding molecules, or are measured indirectly through the subsequent binding of additional, labeling molecules which can bind to, and thereby label, the labeled specific binding molecule. Examples of suitable specific binding molecules are antibodies, antigens, nucleic acids, avidin-biotin, enzyme inhibitors and lectins. A key property of analyte entities is that the analyte entities preferably have two or more specific binding sites which can bind labeled specific binding molecules.

The method of the present invention is generally applicable to many types of specific binding molecules. For example, the method of the invention is illustrated by considering an analyte entity with two distinct epitopes. In the case of labeled specific binding molecules, a sample containing the analyte entity is exposed to two different labeled antibodies, with one antibody specific for each of the two distinct epitopes. Following mixing, if desired, and after waiting for diffusion, encounter and binding of the labeled antibody molecules, the analyte entities have a high probability of being specifically labeled with two labels because of the binding of the two labeled antibodies.

One or more measurements of the amount of label in each bacterium is then made, such that the measurement is capable of resolving the difference of one label from two labels, and other measurements are made which allow the measurement of each bacterium. It is preferred to measure individual bacteria for volume and activity, but in some cases two or more bacteria can be measured together. Such measurement is used to characterize each bacterium.

The measurement process can involve a counting process, the invention provides means for measurements over a large dynamic range of analyte concentrations, that is, from high concentrations to orders of magnitude lower concentrations.

Prior to the carrying out of the process of this invention, two or more labeled specific binding molecules are obtained, using means well known in the art, such that two or more labeled specific binding molecules are prepared, which are capable of binding to two or more binding sites on the analyte. Antibodies which bind to at least two non-overlapping epitopes on the analyte, such that at least two antibodies can be simultaneously and specifically bound to the analyte. Examples of such labeled specific binding molecules include (a) monoclonal antibodies with about one label molecule bound to each antibody molecule, (b) antigen molecules with about one label molecule bound to each antigen entity, (c) monoclonal antibodies with about two label molecules of the same type are bound to each antibody molecule, (d) antigen molecules with about two label molecules of the same type bound to each antigen entity, and (e) polyclonal antibodies containing at least two antibodies capable of binding to at least two non-overlapping epitopes of the analyte entity.

Analyte entities with at least two non-overlapping and non-competing specific binding sites can be measured. The important general class of analyte entities for bacteria include labeled antibodies, antigenic analyte entities capable of independently binding antibodies at two or more different sites can be measured. Examples of such analyte entities with two such sites include all antigens capable of assay by a sandwich assay.

In the general practice of this invention, analyte entities such as microorganisms with a cytochrome system can be measured.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are hereby incorporated by reference.

We claim:

1. A rapid method for the detection, identification and enumeration of respiring microorganisms consisting of
    a) passing a microbial sample through a collecting device to obtain a collected sample;
    b) adding to the collected sample a fluorochrome dye specific for the detection of respiring cells and allowing the dye to incubate;
    c) treating the collected sample with a fluorescent antibody which reacts with a microorganism of interest present in said microbial sample, wherein said fluorescent antibody contrasts said fluorochrome dye specific for the detection of respiring cells;
    d) rinsing away unbound fluorescent antibody;
    e) fixing said collected sample for examination by fluorescence microscopy in which a suitable light system is used to excite the fluorochrome dye and fluorescent antibody to fluoresce; and
    f) quantifying respiring microbial cells.

2. The method of claim 1, wherein said collecting device is selected from the group consisting of a black polycarbonate membrane filter, a reverse flow filter, sedimentation field flow fractionation, and immunomagnetic beads.

3. The method of claim 1, wherein said collecting device is selected from the group consisting of any nonfluorescing filter, a reverse flow or tangential flow filter, an immunocapture device and centrifugation techniques.

4. A rapid method for the detection, identification and enumeration of respiring microbes by the sequential steps of
    a) filtering a sample through a membrane filter to capture microorganisms;
    b) transferring the membrane filter to a pad comprising a fluorochrome dye specific for the detection of respiring cells;
    c) incubating said sample with said fluorochrome dye,
    d) treating the surface of the membrane filter with a fluorochrome labeled antibody which reacts with a specific microbial species or strain of interest present in said sample, and wherein said fluorochrome antibody contrasts said fluorochrome dye specific for the detection of respiring cells;
    e) rinsing unbound fluorochrome labeled antibody from said membrane filter;
    f) fixing said cells of step d) on said membrane filter for examination by fluorescence microscopy in which a suitable light filter system is used to excite the fluorochrome dye and fluorochrome labeled antibody to fluoresce; and
    g) quantifying respiring microbial cells.

5. The method of claim 4, wherein said fluorochrome dye specific for the detection of respiring cells is a tetrazolium compound.

6. The method of claim 4 wherein said fluorochrome dye specific for the detection of respiring microbes is taken up by respiring cells and reduced to insoluble formazan crystals by the cytochrome system of said cells.

7. The method of claim 5, wherein said tetrazolium compound for the detection of respiring microbial cells is 5-Cyano-2,3-Ditolyl Tetrazolium Chloride (CTC).

8. The method of claim 4, wherein said fluorescence microscopy is epifluorescence microscopy.

9. The method of claim 4, wherein said membrane filter is a black polycarbonate membrane filter.

10. A rapid method for the detection, identification and enumeration of respiring microorganisms consisting of
    a) mixing immunomagnetic beads comprising a polymer matrix containing iron, coated with a covalently bound antibody that specifically binds to microbial cells within a liquid sample comprising said microbial cells;
    b) allowing said liquid sample to interact with the beads for up to an hour;
    c) placing the sample in a magnetic separator, which causes the magnetic beads to which cells have attached to separate from the liquid sample;
    d) aspirating the sample, leaving the beads with cells attached;

e) capturing said beads with attached cells on a filter membrane;

f) incubating for 1–3 hours the filter membrane and captured cells with a fluorochrome dye specific for the detection of respiring bacteria;

g) fixing said cells on said membrane filter;

h) treating filter membrane with a specific fluorescent-labeled antibody, wherein said fluorescent-labeled antibody contrasts with said fluorochrome dye specific for detection of respiring cells;

i) rinsing said filter membrane to remove unbound fluorescent labelled antibody;

j) mounting said filter membrane for examination by fluorescence microscopy or laser scanning in which a suitable light filter system is used to excite the fluorochrome dye and fluorochrome-labeled antibody to fluoresce; and k) quantifying respiring microbes.

11. The method of claim 10, wherein said fluorochrome dye specific for the detection of respiring microorganisms is a tetrazolium compound.

12. The method of claim 10, wherein said fluorochrome dye specific for the detection of respiring microorganisms is taken up by respiring cells and reduced to insoluble formazan crystals by the metabolism of said cells.

13. The method of claim 10, wherein said fluorochrome for the detection of respiring microorganisms is 5-Cyano-2,3-Ditolyl tetrazolium Chloride (CTC).

14. A rapid method for the detection, identification and enumeration of respiring microorganisms consisting of a) mixing immunomagnetic beads comprising a polymer core containing iron, coated with a covalently bound antibody that specifically binds to microbial cells with a liquid sample comprising said microbial cells;

b) allowing said liquid sample to interact with the beads for up to an hour, with gentle agitation;

c) placing the sample in a magnetic separator, which causes the magnetic beads to which cells have attached to separate from the liquid sample;

d) aspirating the sample, leaving the beads with cells attached;

e) capturing said beads with attached cells on a non-fluorescing filter membrane;

f) incubating for 1–3 hours the filter membrane with captured cells with a fluorochrome dye specific for the detection of respiring bacteria;

g) fixing said cells on said membrane filter;

h) treating filter membrane with a specific fluorescent labeled antibody, wherein said fluorescent stain or labeled antibody contrasts with said fluorochrome dye specific for detection of respiring cells;

i) rinsing said filter membrane to move unbound fluorescent labelled antibody;

j) mounting said filter membrane for examination by fluorescent microscopy in which a suitable light filter system is used to excite the fluorochrome dye and fluorochrome labeled antibody to fluoresce; and k) quantifying respiring microbes.

15. A rapid method for the detection, identification and enumeration of respiring microorganisms consisting of a) mixing immunomagnetic beads comprising a polymer core containing iron, coated with a covalently bound antibody that specifically binds to microbial cells with a liquid sample comprising said microbial cells;

b) allowing said liquid sample to interact with the beads for up to an hour, with gentle agitation;

c) placing the sample in a magnetic separator, which causes the magnetic beads to which cells have attached to separate from the liquid sample;

d) aspirating the sample, leaving the beads with cells attached;

e) capturing said beads with attached cells on a non-fluorescing filter membrane;

f) incubating for 1–3 hours the filter membrane with captured cells with a fluorochrome dye specific for the detection of respiring bacteria;

g) fixing said cells on said membrane filter;

h) treating filter membrane with a specific fluorescent labeled antibody, wherein said fluorescent stain or labeled antibody contrasts with said fluorochrome dye specific for detection of respiring cells;

i) rinsing said filter membrane to move unbound fluorescent labelled antibody;

j) mounting said filter membrane for examination by fluorescent microscopy in which a suitable light filter system is used to excite the fluorochrome dye and fluorochrome labeled antibody to fluoresce; and k) quantifying respiring microbes, wherein said method is automated with laser scanning or flow cytometry.

16. A rapid method for the detection, identification and enumeration of respiring microorganisms consisting of a) mixing immunomagnetic beads comprising a polymer core containing iron, coated with a covalently bound antibody that specifically binds to microbial cells with a liquid sample comprising said microbial cells;

b) allowing said liquid sample to interact with the beads for up to an hour, with gentle agitation;

c) placing the sample in a magnetic separator, which causes the magnetic beads to which cells have attached to separate from the liquid sample;

d) aspirating the sample, leaving the beads with cells attached;

e) capturing said beads with attached cells on a non-fluorescing filter membrane;

f) incubating for 1–3 hours the filter membrane with captured cells with a fluorochrome dye specific for the detection of respiring bacteria;

g) fixing said cells on a filter membrane;

h) treating filter membrane with a specific fluorescent labeled antibody, wherein said fluorescent stain or labeled antibody contrasts with said fluorochrome dye specific for detection of respiring cells;

i) rinsing said filter membrane to move unbound fluorescent labelled antibody;

j) mounting said filter membrane for examination by fluorescent microscopy in which a suitable light filter system is used to excite the fluorochrome dye and fluorochrome labeled antibody to fluoresce; and k) quantifying respiring microbes, wherein a collecting device to capture the microbial cells from contaminated sample comprises a centrifuge for sedimentation field flow fractionation or a tangential flow separation system.

17. The assay according to claim 1, wherein said rapid assay is performed in a time range of 3–6 hours.

18. The assay according to claim 4, wherein said rapid assay is performed in a time range of 3–6 hours.

19. The assay according to claim 10, wherein said rapid assay is performed in a time range of 3–6 hours.

* * * * *